(12) United States Patent
Langer et al.

(10) Patent No.: US 9,994,615 B2
(45) Date of Patent: Jun. 12, 2018

(54) SELF-REGULATED PEPTIDE HYDROGEL FOR INSULIN DELIVERY

(71) Applicants: Massachusetts Institute of Technology, Cambridge, MA (US); The Children's Medical Center Corporation, Boston, MA (US)

(72) Inventors: Robert S. Langer, Newton, MA (US); Daniel G. Anderson, Sudbiry, MA (US); Zhen Gu, Cambridge, MA (US); Alex Arthur Aimetti, Waltham, MA (US)

(73) Assignees: Massachusetts Institute of Technology, Cambridge, MA (US); The Children's Medical Center Corporation, Boston, MA (US)

( * ) Notice: Subject to any disclaimer, the term of this patent is extended or adjusted under 35 U.S.C. 154(b) by 0 days. days.

(21) Appl. No.: 14/379,477

(22) PCT Filed: Feb. 19, 2013

(86) PCT No.: PCT/US2013/026632
§ 371 (c)(1),
(2) Date: Aug. 18, 2014

(87) PCT Pub. No.: WO2013/123491
PCT Pub. Date: Aug. 22, 2013

(65) Prior Publication Data
US 2015/0025005 A1    Jan. 22, 2015

Related U.S. Application Data

(60) Provisional application No. 61/600,397, filed on Feb. 17, 2012.

(51) Int. Cl.
| | |
|---|---|
| *A61K 38/28* | (2006.01) |
| *A61K 9/00* | (2006.01) |
| *A61K 38/00* | (2006.01) |
| *C07K 7/06* | (2006.01) |
| *A61K 9/06* | (2006.01) |
| *A61K 47/42* | (2017.01) |

(52) U.S. Cl.
CPC ............... *C07K 7/06* (2013.01); *A61K 9/0019* (2013.01); *A61K 9/06* (2013.01); *A61K 38/28* (2013.01); *A61K 47/42* (2013.01); *A61K 38/00* (2013.01)

(58) Field of Classification Search
CPC .......... C07K 7/06; A61K 9/0019; A61K 9/06; A61K 38/28; A61K 47/42; A61K 38/00
See application file for complete search history.

(56) References Cited

U.S. PATENT DOCUMENTS

| | | | |
|---|---|---|---|
| 4,364,385 A | 12/1982 | Lossef | |
| 5,670,483 A | 9/1997 | Zhang | |
| 6,410,053 B1 | 6/2002 | Taylor | |
| 6,548,630 B1 | 4/2003 | Zhang | |
| 7,098,028 B2 * | 8/2006 | Holmes | ................ C07K 5/0815 |
| | | | 435/325 |
| 2003/0186846 A1 | 10/2003 | Hoeg-Jensen | |
| 2010/0029545 A1 | 2/2010 | Sumerlin et al. | |

FOREIGN PATENT DOCUMENTS

| | | | | |
|---|---|---|---|---|
| WO | 199501186 | | 1/1995 | |
| WO | WO 95/01186 | * | 1/1995 | ............. A61K 47/36 |
| WO | WO /95/012286 | * | 1/1995 | |
| WO | 2007142757 | | 12/2007 | |

OTHER PUBLICATIONS

Thomas Hoeg-Jensen et al: "Reversible Insulin Self-Assembly under Carbohydrate Control", Journal of the American Chemical Society, vol. 127, No. 17, May 1, 2005 (May 1, 2005), pp. 6158-6159.*
Wang et al., Effects of the sequence and size of non-polar residues on self-assembly of amphiphilic peptides, International Journal of Biological Macromolecules 36 (2005) 232-240.*
Ozbas et al., Semiflexible Chain Networks Formed via Self-Assembly of β-Hairpin Molecules, PRL 93, 268106 (2004).*
Sigma-Aldrich Amino Acid Chart, 3 pages, 2014.*
Hauser and Zhang, Designer Self-Assembling Peptide Materials for Diverse Applications, Macromol. Symp. 2010, 295, 30-48.*
Koutsopoulos et al., Controlled release of functional proteins through designer self-assembling peptide nanofiber hydrogel scaffold, PNAS Mar. 24, 2009 vol. 106 No. 12 pp. 4623-4628.*
Kopeček and Yang, Peptide-directed self-assembly of hydrogels, Acta Biomater. Mar. 2009; 5(3):805-816.*
Hartgerink and Stupp, Self-Assembly and Mineralization of Peptide-Amphiphile Nanofibers, Science, Science 294 (5547), 1684-1688, 2001.*
Zhang et al., Amino Acids, Pept. Proteins, 2012, 37, 40-65.*
Hartgerink et al., Science, Nov. 23, 2001, vol. 294, pp. 1684-1688.*
Hauser and Zhang, Macromol. Symp. 295, 30-48 (2010).*
Ravaine, et al., J. Controlled Rel. 132, 2-11 (2008).*
Hartgerink, et al., "Self-assembly and mineralization of peptide-amphiphile nanofibers", Science, 294:168-8 (2001).

(Continued)

*Primary Examiner* — Karlheinz R. Skowronek
*Assistant Examiner* — Joseph Fischer
(74) *Attorney, Agent, or Firm* — Pabst Patent Group LLP (57) ABSTRACT

A glucose binding amphiphilic peptide hydrogel insulin delivery system that is responsive to glucose concentrations under physiological conditions is provided. Insulin is encapsulated in a glucose binding hydrogel, made from self-assembling amphiphilic peptides including a hydrophobic domain including a beta sheet forming region coupled to a charged hydrophilic domain modified to contain a glucose binding segment. The formulations are designed to release insulin as a function of blood glucose level, maintaining the patients' blood glucose level in an optimum range and avoiding both hyper- and hypoglycemia.

22 Claims, 3 Drawing Sheets

(56) References Cited

OTHER PUBLICATIONS

Hisamitsu, et al., "Glucose-responsive gel from phenylborate polymer and poly(vinyl alcohol): prompt response at physiological pH through the interaction of borate with amino group in the gel", Pharm Res., 14:289-93 (1997).
Hoare and Pelton, "Change-switching amphoteric glucose-responsive microgels with physiological swelling activity", Biomacromolecules, 9(2):733-40 (2008).
Hoeg-Jensen, et al., "Reversible insulin self-assembly under carbohydrate control", J Am Chem Soc., 127(17):6158-9 (2005).
Kumareswaran, et al., "Artificial pancreas: an emerging approach to treat Type 1 diabetes", Expert Rev Med Devices, 6:401-10 (2009).
Liang and Liu, "A self-assembled molecular team of boronic acids at the gold surface for specific capture of cis-diol biomolecules at neutral pH", Chem Commun (Camb)47:2255-7 (2011).
Matsumoto, et al., "A totally synthetic glucose responsive gel operating in physiological aqueous conditions", Chem. Commun., 46:2203-5 (2010).
Matsumoto, et al., "Glucose-responsive polymer bearing a novel phenylborate derivative as a glucose-sensing moiety operating at physiological pH conditions", Biomelecules, 4(5):1410-6 (2003).
Ravaine, et al., "Chemically controlled closed-loop insulin delivery", J Cont Rel., 132(1):2-11 (2008).
Ren, et al., "Ring-opening polymerization with synergistic co-monomers: access to a boronate-functionalized polymeric monolith for the specific capture of cis-diol-containing biomolecules under neutral conditions", Angew Chem Int Ed Engl., 48:6704-7 (2009).
Yang, et al., "Designer self-assembling peptide nanomaterials", Nano Today, 4:193-210 (2009).

\* cited by examiner

SEQUENCE LISTING

```
<160> NUMBER OF SEQ ID NOS: 2

<210> SEQ ID NO 1
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 1

Ala Glu Ala Glu Ala Lys Ala Lys Ala Glu Ala Glu Ala Lys Ala Lys
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 2

Arg Ala Arg Ala Asp Ala Asp Ala Arg Ala Arg Ala Asp Ala Asp Ala
1               5                   10                  15
```

SELF-REGULATED PEPTIDE HYDROGEL FOR INSULIN DELIVERY

CROSS-REFERENCE TO RELATED APPLICATIONS

This application is an application under 35 U.S.C. § 371 of copending PCT Application No. PCT/US2013/026632, filed Feb. 19, 2013, which claims benefit of U.S. Provisional Application No. 61/600,397, filed Feb. 17, 2012.

FIELD OF THE INVENTION

The present invention generally relates to formulations containing insulin in a glucose binding hydrogel for the treatment of diabetes.

STATEMENT REGARDING FEDERALLY SPONSORED RESEARCH

The U.S. government has no rights in this invention.

REFERENCE TO SEQUENCE LISTING

The Sequence Listing submitted on Feb. 9, 2016, as a text file named "MIT 15056_ST25.txt," created on Oct. 10, 2015, and having a size of 847 bytes is hereby incorporated by reference pursuant to 37 C.F.R § 1.52(e)(5).

BACKGROUND OF THE INVENTION

Diabetes mellitus is a disorder of glucose regulation with accumulation of glucose in the blood. In normal individuals, insulin is secreted basally, usually in the range of 0.5 to 1.0 units per hour, and the levels are increased after a meal. Responsive to the rise in blood glucose levels following a meal, the pancreas secretes a bolus of insulin, which returns blood glucose to normal levels by stimulating the uptake of glucose into cells and signaling the liver to reduce glucose production. There are normally two phases of insulin release in response to a meal. The early phase (responsible for shutting down hepatic glucose production) is a spike of insulin release that occurs within 2-15 minutes of eating. The late phase release extends about 2 hours. Between meals the liver breaks down glycogen stores to provide glucose to the brain and other tissues.

Diabetes results in chronic hyperglycemia due to the inability or reduced ability of the pancreas to produce adequate amounts of insulin or due to the inability or reduced ability of cells to synthesize and/or release the insulin required. In diabetics, the effectiveness of the first-phase response is decreased or absent, leading to elevated postprandial glucose levels. Diabetes is a major public health problem affecting 285 million people across the world and this number is expected to be over 450 million by 2030 (Wild, et al., *Diabetes Care*, 27: 1047-1053 (2004). The malfunction of glucose regulation arises from 1) insufficient secretion of insulin due to autoimmune-mediated destruction of pancreatic f3-cells (type 1 diabetes) or 2) disorders of both insulin resistance and secretion (type 2 diabetes) (Pickup, et al., *Diabetes Metab Res Rev*, 24: 604-610 (2008); Stumvoll, et al. *Lancet*, 365:1333-1346 (2005); and Kahn, *Diabetes* 43:1066-1084 (1994).

Multiple subcutaneous insulin injections and regular monitoring of blood glucose levels are essential to sustain life for type 1 diabetic patients and some type 2 diabetic patients (Owens, et al., *Lancet*, 358:739-746 (2001)). However, such self-administration is painful and requires an indispensable commitment of patients. More importantly, this treatment, known as open-loop insulin delivery, does not maintain normoglycemia due to highly dynamic blood glucose concentrations (Jeandidier, et al., *Adv Drug Deliv Rev*, 35:179-198 (1999); Owens, et al., *Nat Rev Drug Discov*, 1:529-540 (2002)). Lack of tight control over glucose concentrations closer to the normal level accounts for many chronic complications such as limb amputation, blindness and kidney failure and often resulted in risks of fatal hypoglycemia (*N Engl J Med.*, 329:977-986 (1993)). Therefore, a pancreas-like, synthetic closed-loop device able to continuously and intelligently release insulin in response to blood glucose levels is highly desirable (Kumareswaran, et al. *Expert Rev Med Devices*, 6:401-410 (2009); Ravaine, et al., *J. Control Release*, 132:2-11 (2008)).

A straightforward strategy is to integrate a glucose monitoring moiety and a sensor-triggered insulin releasing moiety into one system. To date, a number of glucose-responsive formulations and devices have been explored, mainly derived from three categories: 1) glucose oxidase (GOx) based enzymatic reaction-induced response systems; 2) lectin binding protein Concanavalin A (Con A) based response systems and 3) phenylboronic acid (PBA) based synthetic glucose-binding systems (Ravaine, et al., *J. Control Release* 132:2-11 (2008)).

A GOx based system is described in U.S. Pat. No. 4,364,385 to Lossef, et al., which is made of a compartment limited by a semipermeable, ionically charged membrane, containing glucose oxidase and catalase. U.S. Pat. No. 6,410,053 to Taylor discloses insulin immobilized in a dextran/concavalin A matrix, which can reversibly bind glucose and release insulin in response to changing glucose concentrations.

PBA is boronic acid containing a phenyl substituent and two hydroxyl groups attached to boron. PBA and its derivatives have the ability to form complexes with polyol molecules such as glucose, and fructose, in aqueous solution. PBA can form stable hydrogels with a polyol, such as poly(vinyl alcohol) (Hisamitsu, et al., *Pharm Res* 14:289-293 (1997)). The ability of PBA to bind polyols has been exploited in different ways to provide a glucose binding insulin delivery system. Hydrogels obtained from N-isopropylacrylamide (NIPAM) and PBA swelled and shrank according to the glucose concentration at pH 9. This system was modified to operate at physiological pH conditions by modifying the chemical structure of the receptor with an electron-withdrawing group on the phenyl ring. Matsumoto, et al., *Biomolecules*, 4(5):1410-6 (2003)). Other researchers have directly coupled a PBA moiety to insulin, to provide glucose binding insulin. For example, U.S. Publication No. 20030186846 by Hoeg-Johnson, et al., discloses an insulin delivery system made of insulin derivatives with a built in glucose sensor, such as an aryl boronate moiety.

These glucose insulin delivery systems have several limitations. The protein-involved platforms are not active for long periods due to denaturation under physiological conditions. The GOx based reaction needs additional dissolved oxygen. ConA exhibits significant cytotoxicity. These limit their implantable applications (Ravaine, et al., *J. Control Release* 132:2-11 (2008)). For PBA systems, the challenge remains to design devices that function in response to glucose at or near physiological pH. Moreover, formation of responsive biomaterials or relevant units requires synthetic polymerization (Ravaine, et al., *J. Control Release* 132:2-11 (2008)).

It is therefore an object of this invention to provide a PBA based insulin delivery system that is responsive to changing glucose concentrations at or near physiological pH.

It is also an object of the present invention to provide a method of making a PBA based glucose sensitive insulin delivery system that is responsive to glucose concentrations at or near physiological pH.

It is a further objection of the present invention to provide a method of controlling blood glucose levels in a patient in need thereof, by administering a PBA based insulin delivery system which responds to changing insulin concentrations at physiological pH.

SUMMARY OF THE INVENTION

A PBA based glucose sensitive insulin delivery system that is responsive to glucose concentrations at or near physiological pH is provided. Insulin is encapsulated in a glucose binding hydrogel. The glucose binding hydrogel is made from self-assembling amphiphilic peptides, modified to contain a glucose binding segment. In one embodiment, the amphiphilic peptide has a hydrophobic region operably linked to a hydrophilic region via a beta-sheet forming segment. In another embodiment, the beta-sheet forming segment is covalently attached to the N-terminus of the hydrophilic region and the hydrophobic region is covalently attached to the N-terminus of the beta-sheet forming region. A glucose binding moiety is attached to the hydrophobic region, for example, at the terminus of the hydrophobic region. The glucose binding moiety is preferably a boronate, for example, phenyl boronate. The hydrophobic region preferably includes a mono or dialkyl group. The hydrophilic segment includes charged amino acids, preferably lysine residues. These self assemble to form a gel.

The gel has entrapped therein insulin alone or in combination with another pharmaceutically active agent. The formulations are designed to release insulin as a function of blood glucose level, maintaining the patients' blood glucose levels in an optimum range and avoiding both hyper- and hypoglycemia. When glucose binds to the glucose binding moiety, the conformation of the molecule changes and/or the gel becomes more unstable, releasing insulin. When the glucose level in the tissue decreases, the glucose dissociates from the glucose binding moiety, causing the gel to become more stable and stop releasing all or some of the insulin.

The gel formulation provides a method for controlling blood glucose levels in a subject in need thereof. The formulation may be for subcutaneous, intradermal or intramuscular administration, preferably subcutaneous injection.

DETAILED DESCRIPTION OF THE INVENTION

I. Definitions

"Controlling blood glucose levels" refers to the maintenance of blood glucose concentrations at a desired level, typically between 70-130 mg/dL or 90-110 mg/dL.

"Dosage unit form" as used herein refers to a physically discrete unit of conjugate appropriate for the patient to be treated.

"Hydrophilic," as used herein, refers to molecules which have a greater affinity for, and thus solubility in, water as compared to organic solvents. The hydrophilicity of a compound can be quantified by measuring its partition coefficient between water (or a buffered aqueous solution) and a water-immiscible organic solvent, such as octanol, ethyl acetate, methylene chloride, or methyl tert-butyl ether. If after equilibration a greater concentration of the compound is present in the water than in the organic solvent, then the compound is considered hydrophilic.

"Hydrophobic," as used herein, refers to molecules which have a greater affinity for, and thus solubility in, organic solvents as compared to water. The hydrophobicity of a compound can be quantified by measuring its partition coefficient between water (or a buffered aqueous solution) and a water-immiscible organic solvent, such as octanol, ethyl acetate, methylene chloride, or methyl tert-butyl ether. If after equilibration a greater concentration of the compound is present in the organic solvent than in the water, then the compound is considered hydrophobic.

"Hydrogel," as used herein, refers to a gelatinous colloid, or aggregate of polymeric molecules in a finely dispersed semi-solid state, where the polymeric molecules are in the external or dispersion phase and water (or an aqueous solution) is forms the internal or dispersed phase. Generally, hydrogels are at least 90% by weight of an aqueous solution. "Nanofiber" refers to a fiber having a diameter of nanoscale dimensions. Typically a nanoscale fiber has a diameter of 500 nm or less.

"Nanofiber" refers to a fiber having a diameter of nanoscale dimensions. Typically a nanoscale fiber has a diameter of 500 nm or less.

"Peptide," as used herein includes "polypeptide," "oligopeptide," and refers to a chain of at α-amino acid residues linked together by covalent bonds (e.g., peptide bonds). The length of the peptide is limited at the lower end only by the minimum number amino acids required to form a self-assembling peptide.

"Pharmaceutically acceptable carrier" as used herein means a non-toxic, inert solid, semi-solid or liquid filler, diluent, encapsulating material or excipient. Remington's Pharmaceutical Sciences Ed. by Gennaro, Mack Publishing, Easton, Pa., 1995 discloses various carriers used in formulating pharmaceutical compositions and known techniques for the preparation thereof.

"Self-assembling", as used herein, refers to the spontaneous or induced assembly of molecules into defined, stable, noncovalently bonded assemblies that are held together by intermolecular forces.

II. Compositions

A hydrogel platform is provided for intelligent delivery of insulin through self-assembled peptide nanofibers with glucose binding sites. The hydrogel is formed from self-assembling peptides. The peptides include a hydrophobic domain and a beta-sheet forming domain which provides hydrogen bonding affinity between adjacent peptide units and promotes formulation of bulk hydrogel.

When the peptides are placed under physiological conditions (approximately pH 7-7.5, normal saline, room to body temperature of about 22-37° C.), they self-assemble to form nanofibers which entwine and physically crosslink to form a gel. A drug to be delivered, in this case, insulin or an insulin analog, is entrapped within the gel. When the glucose-binding moiety binds glucose, the shape and structure of the hydrogel changes, allowing entrapped drug to be released. Binding of glucose is a function of the concentration of the glucose in the tissue, with more glucose binding when tissue concentrations are elevated and less glucose binding when tissue concentrations are low. This provides for "smart" or "responsive" release in situ of the insulin.

Insulin release through the hydrogel additionally can be controlled by varying the peptide nanofiber density, which in turn can be controlled by varying the amphiphilic peptide concentrations.

A. Self-Assembling Peptide Components

Figure 1A:
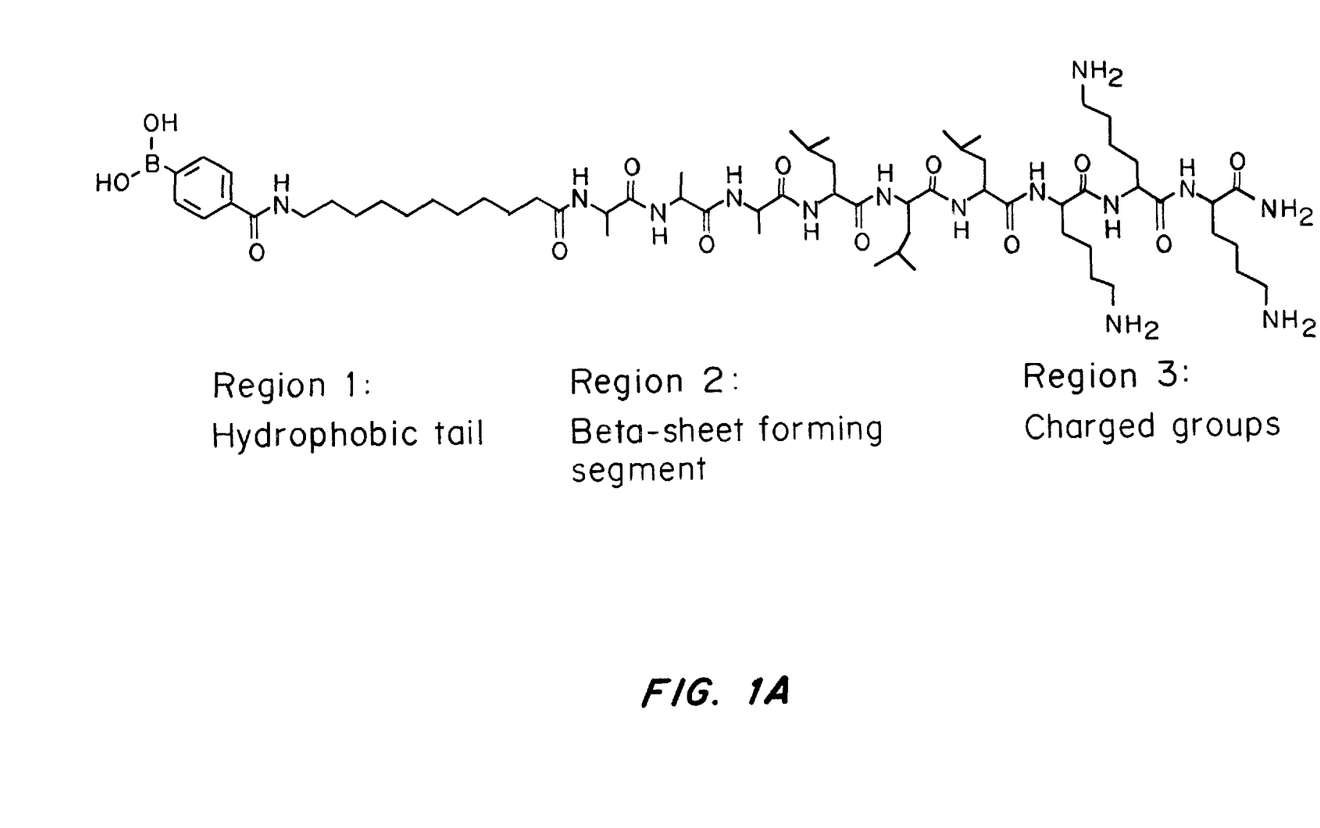
FIG. 1A is a schematic showing the structure of an amphiphile-containing a phenylboronic acid-modified N-terminus.

The self-assembling peptides include a hydrophobic region operably linked to a hydrophilic region via beta-sheet forming segment. An exemplary self-assembling peptide is shown in FIG. 1A. In preferred embodiments, the beta-sheet forming segment is covalently attached to the hydrophilic region and the hydrophobic region is covalently attached to the beta-sheet forming segment. The hydrophilic region contains a charged segment, preferably formed of charged amino acids.

Useful peptides can vary in length, so long as they retain the ability to self-assemble. The number of amino acid residues in the peptide segments may range from as few as 2 to about 200 α-amino acid residues. Typically, peptides which self-assemble have from about 6 to about 200 residues, preferably from about 6 to about 64 residues, more preferably from about 8 to about 36 residues, most preferably from about 8 to about 24 residues.

Self-assembling peptide amphiphiles described in Hartgerink, et al. Science 294:1683-1688, (2001), can be modified as described herein to include a glucose binding component and beta sheet forming segments.

In some embodiments the nanofibers formed from the peptides have a diameter of 100 nm or less, 50 nm, 20 nm or less, a diameter of between 10 and 20 nm, between 5 and 10 nm, or less than 5 nm. The ranges listed are assumed to include both endpoints. The fibers are formed by the peptides. Those fibers (or cylindrical micelles) are formed by the combination of hydrogen-bonding between beta-sheet forming amino acids and hydrophobic collapse of the tails. By changing pH or adding counterions to screen the charged surfaces of fibers, hydrogels can be formed.

(1) Hydrophobic Region

In preferred embodiments, the hydrophobic region is covalently attached to the N-terminus of the beta-sheet forming segment. The hydrophobic region can contain one or more alkyl groups. The hydrophobic region preferably contains one or two $C_{6\ or\ greater}$. Traditionally, fatty acid tails, typically C6 and greater alkyl chains, are exclusively used. This simple, linear hydrophobic unit contributes to the facile self-assembly under physiological conditions, as opposed to alternative hydrophobic monomers/polymers.

(2) Beta-Sheet Forming Segment

The self-assembling peptide can include a hydrophobic domain including side chains or amino acids forming a beta sheet structure.

In a preferred embodiment, the β-sheet forming segment preferably includes amino acids which can interact to form beta sheets. In one embodiment the amino acids are amino acids that have hydrophobic side chains under physiological conditions. Suitable amino acids include, but are not limited to, glycine, alanine, valine, leucine, and isoleucine, and other non-naturally occurring amino acids which may be used in a similar chemical and structural manner in the peptide amphiphile. The number of amino and type of amino can vary so long as they retain the ability to form beta sheets. There number of amino acids can be from about 4 to about 10 amino acids in this segment and most preferably about 6 amino acids.

In other embodiments, the beta sheet forming segment can contain hydrophilic polar amino acid residues and hydrophobic non-polar amino acid residues under physiological conditions. The one or more hydrophilic residues can alternate with one or more hydrophobic residues. This segment can include alternating amino acid sequences known to self-assemble and to form beta sheet scaffolds (reviewed in Yang, et al., Nano Today, 4:193-210 (2009)). For example, the ionic self-complementary peptides that form stable beta-sheet structures in water and undergo spontaneous assembly to form nanofiber include EAK16 (AEAEAKAKAEAEAKAK (SEQ ID NO:1)) and RAD16 (RARADADA RARADADA (SEQ ID NO:2)). The self-assembly event creating peptide scaffolds takes place under physiological conditions of neutral pH and milli-molar salt concentrations.

U.S. Pat. Nos. 5,670,483, 6,548,630, and 7,098,028 by Zhang et al. describe amphiphilic peptides having alternating hydrophobic and hydrophilic residues. WO 2007/142757 describes compositions including peptides with alternating hydrophilic and hydrophobic monomers that allow them to self-assemble under physiological conditions are formulated for application to wounds. Such self-assembling peptides can be modified as described herein to provide glucose binding self-assembling peptides.

(3) The Charged Segment

The charged segment enhances solubility of the peptide amphiphile in an aqueous environment. In experiments, gels were formed from a peptide precursor solution of 1 wt % (10 mg/mL). However, in general, to form mechanically stronger gels, higher solubility, thus higher initial wt %, is required. This can be enhanced by addition of charged/hydrophilic amino acids. To form hydrogels, the peptide should be dissolved in aqueous solution to form fibers and then gelled by changing pH or adding counterions to screen the charged surfaces of fibers. The charged peptide segment includes amino acids which provide the requisite solubility and permit self-assembly. Since the two regions, hydrophobic and beta-sheet, contribute to poor peptide solubility in aqueous solutions, the charged/hydrophilic segment is needed to enhance the solubility. There is no exact amino acid ratio that is required between charged and hydrophobic regions. There may be from about 2 to about 7 amino acids, and preferably there are about 3 or 4 amino acids, in this segment. In a preferred embodiment, the charged domain (hydrophilic) contains lysine residues. The free amines from lysines in this peptide structure coordinate with adjacent boronic acid to generate Wulff-type boronic acid, which has enhanced affinity at neutral pH (Ren, et al., *Angew Chem Int Ed Engl* 48, 6704-6707 (2009); Liang, et al., *Chem Commun (Camb)* 47:2255-2257 (2011).

This segment is attached at a first end to the beta sheet forming segment. A spacer group peptide may also be included into the peptide amphiphile.

(4) Glucose Binding Component

The self-assembling peptide is modified at the hydrophobic tail to include a chemical group capable of binding to or reacting with glucose. Examples of reversible glucose sensors are organic borates, preferably aryl boronates or other borates. Boronic acids covalently react with cis-diols to form five or six membered cyclic esters in an alkaline aqueous solution, which dissociates in acidic pH.

Boronate sensors that bind glucose under physiological conditions are preferred. Examples of useful boronates include, but are not limited to, aryl boronates, aminomethyl-aryl-2-boronates, and other boronates with amino groups in the vicinity or aryl boronates substituted with electron-withdrawing groups for example, sulfo-, carboxy-, nitro-, cyano-, fluoro-phenyl boronates, pyridine boronates, pyridinium boronates or their combinations. Diboronates may be employed to provide glucose selectivity over for instance fructose and lactate.

In a preferred embodiment, the hydrophilic domain of the self-assembling peptide is terminated with phenylboronic acid (PBA). The PBA structure can be designed to bind glucose at a physiological value. The pKa of traditional phenylboronic acid is approximately 8.9. However, the PBA conjugate is chemically modified to lower the pK to less than 8.9 (Matsumoto A. et al., *Chem. Commun.*, 2010, 46, 2203-2205). Based on this value, only a limited percentage of PBA should be able to covalently bind glucose at physiological pH. However, based on the results, there is sufficient glucose interaction to disrupt the peptide nanofibers.

Figure 1B:
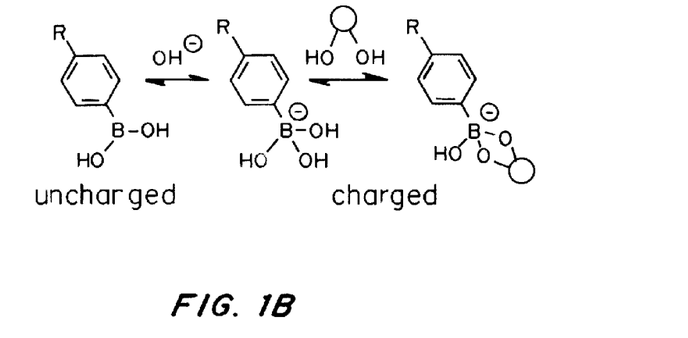
FIG. 1B is a schematic showing glucose-dependent equilibria of (alkylamido)phenylboronic acid (PBA).
Figure 1C:
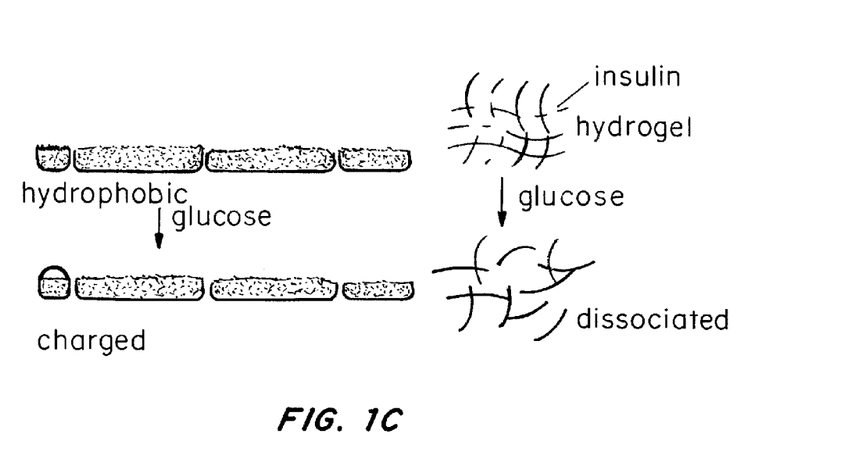
FIG. 1C is a schematic mechanism of self-regulated insulin release from the self-assembled hydrogel.
Figure 3:
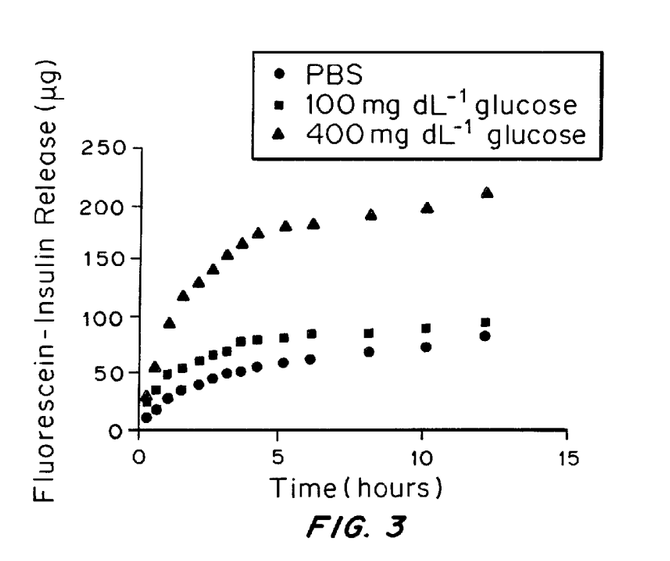
FIG. 3 is a graph showing in vitro accumulated release of insulin over time in 1×PBS solutions of different glucose concentrations, 0, 100 and 400 mg/dL.

The original PBA decorated segment is neutral, hydrophobic and expected to facilitate formation of hydrogels. The phenylboronic acid moieties are in equilibrium between the charged (anionic) and uncharged form as shown in FIG. 1B. Only charged phenylboronic acid moieties can form a stable complex with glucose. The complex between the uncharged form and glucose is unstable because of its high susceptibility to hydrolysis. When the charged phenylboronic acid moieties form complexes with glucose, the equilibrium is shifted in the direction of increasing charged phenyl boronic acid groups. The increasing negative charge on the PBA groups results in disruption of the secondary structure causing the gel to dissociate and release encapsulated insulin (FIG. 1*b,c*). Therefore, the rate of such therapeutic release adapts to glucose level fluctuations As shown in FIG. 3, the amount of negatively charged PBA is increased with the increase of the glucose level, which results in the dissociation of hydrogel and subsequent increase of the rate of the therapeutic release.

B. Pharmaceutically Active Agents (1) Insulin

The amphiphilic peptide hydrogels can be used to deliver one or more pharmaceutical agents. In a preferred embodiment, the pharmaceutical agent is insulin. Any insulin or insulin analog may be included in the formulation. Typically the formulation contains from 5 to 1,000 U of insulin/ml of formulation, preferably 100 U of insulin/ml of formulation, typically, the formulation contains greater than 20 U of insulin/ml of the formulation. Preferably, the amount of insulin is effective to control the recipient's blood glucose levels.

The concentration of insulin can be tailored. The gel solely acts as a depot to store insulin and glucose aids in the disruption of peptide structure to enhance the release of insulin. That is an inherent advantage of a controlled insulin release vehicle. Significantly higher dosages can be loaded into the gel than what is normally used to treat a patient since the protein is rendered unavailable, or 'inactive', by encapsulation within the device.

The insulin in the formulation may be human insulin, recombinant human insulin, insulin from a non-human animal source (e.g. bovine, porcine) or any other insulin, including insulin analogs. The insulin formulations can include mixtures of different insulins to the extent they are compatible.

"Insulin" refers to a natural peptide hormone made by the pancreas that controls the level of the sugar glucose in the blood. Insulin permits cells to use glucose.

Fast Acting Insulins

Fast acting insulins start to work within one to 20 minutes, peaking about one hour later and lasting from three to five hours. Fast acting insulin takes about two hours to fully absorb into the systemic circulation. Fast acting insulins include regular recombinant human insulin (such as HUMULIN® marketed by Lilly, and NOVOLIN®, marketed by NovoNordisk) which are administered in an isotonic solution at pH 7. Bovine and porcine insulins, which differ in several amino acids to human insulin, but are bioactive in humans, are also fast acting insulins.

"Insulin analog", as used herein, refers to human insulin in which one or more amino acid residues have been replaced by another amino acid residue or deleted or in which the A chain and/or the B chain has been extended by addition of one or more amino acid residues at the N-terminal or at the C-terminal and which controls the level of glucose in the blood but with different pharmacokinetics than the naturally occurring insulin.

Lispro.

Eli Lilly and Company had the first insulin analogue with "lispro", a rapid acting insulin analogue. It is marketed under the trade name HUMALOG®. It is engineered through recombinant DNA technology so that the penultimate lysine and proline residues on the C-terminal end of the B-chain are reversed. This modification does not alter the insulin receptor binding, but blocks the formation of insulin dimers and hexamers. This allows larger amounts of active monomeric insulin to be available for postprandial (after meal) injections.

Rapid Acting Insulin

This group include insulins that have been modified or have altered locations of amino acids in order to enhance their rate of absorption. There are three types of rapid-acting commercial insulin analogs available: lispro insulin (Lysine-Proline insulin, sold by Eli Lilly as HUMALOG®), glulisine insulin (sold by Sanofi-Aventis as APIDRA® and aspart insulin (sold by Novo Nordisk as NOVOLOG®).

Aspart.

Novo Nordisk markets "Aspart" as NOVOLOG/NOVORAPID® (UK-CAN) as a rapid acting insulin analogue. It is created through recombinant DNA technology so that the amino acid, B28, which is normally proline, is substituted with an aspartic acid residue. This analogue also prevents the formation of hexamers, to create a faster acting insulin. It is approved for use in CSII pumps and FLEXPEN® and NOVOPEN® delivery devices for subcutaneous injection.

Glulisine.

Glulisine is a rapid acting insulin analog from Sanofi-Aventis, approved for use with a regular syringe, in an insulin pump or the OPTICLIK® Pen. Standard syringe delivery. It is sold under the name APIDRA®. The FDA-approved label states that it differs from regular human insulin by its rapid onset and shorter duration of action.

Intermediate Acting Insulins

Intermediate-acting insulin has a longer lifespan than short-acting insulin but it is slower to start working and takes longer to reach its maximum strength. Intermediate-acting insulin usually starts working within 2-4 hours after injection, peaks somewhere between 4-14 hours and remains effective up to 24 hours. Types of intermediate-acting insulin include NPH (Neutral Protamine Hagedorn) and LENTE® insulin. NPH insulin contains protamine which slows down the speed of absorption so that the insulin takes longer to reach the bloodstream but has a longer peak and lifespan.

Shifted Isoelectric Point Insulins

Normal unmodified insulin is soluble at physiological pH. Analogues have been created that have a shifted isoelectric point so that they exist in a solubility equilibrium in which most precipitates out in the tissue then slowly dissolves into the bloodstream and is eventually excreted by the kidneys. These insulin analogues are used to replace the basal level of insulin, and may be effective over a period of up to 24 hours.

Glargine Insulin.

Sanofi-Aventis developed glargine as a longer lasting insulin analogue, and markets it under the trade name Lantus®. It is created by modifying three amino acids. Two positively charged arginine molecules are added to the C-terminus of the B-chain, and shift the isoelectric point from 5.4 to 6.7, making glargine more soluble at a slightly acidic pH and less soluble at a physiological pH. Replacing the acid-sensitive asparagine at position 21 in the A-chain by glycine avoids deamination and dimerization of the arginine residue. These three structural changes and formulation with zinc result in a prolonged action when compared with biosynthetic human insulin. When the pH 4.0 solution is injected, most of the insulin precipitates and is sequestered in subcutaneous tissue. Small amounts of the precipitated material dissolve into solution in the bloodstream, and the basal level of insulin is maintained up to 24 hours. The onset of action of subcutaneous insulin glargine is somewhat slower than NPH human insulin.

Detemir Insulin.

Novo Nordisk created insulin detemir and markets it under the trade name LEVEMIR® as a long-lasting insulin analogue for maintaining the basal level of insulin. The basal level of insulin may be maintained for up to 20 hours, but the time is clearly affected by the size of the injected dose. This insulin has a high affinity for serum albumin, increasing its duration of action.

Long Acting Insulins

Long acting insulins include Eli Lilly's Humulin® U (Ultralente® human insulin (recombinant DNA origin) extended zinc suspension); and insulin glargine (Lantus® Aventis). Insulin glargine is a recombinant human insulin analog that can have up to 24 hour duration. It differs from human insulin by having a glycine instead of asparagine at position 21 and two arginines added to the carboxy-terminus of the beta-chain. LANTUS® consists of insulin glargine dissolved in a clear aqueous fluid (100 IU, 3.6378 mg insulin glargine, 30 micrograms zinc, 2.7 mg m-cresol, 20 mg glycerol 85%, and water to 1 ml).

(2) Other Pharmaceutically Active Agents

Insulin may be administered alone or in combination with other pharmaceutical agents. Examples of agents that can be delivered in combination with insulin include including peptides, proteins, nucleotide molecules (RNA sequences, DNA sequences), sugars, polysaccharides, and small organic molecules. Preferably, the active agent is at least slightly soluble in aqueous medium (i.e. 10,000 parts of aqueous solvent per solute), and more preferably is highly soluble in aqueous medium. Suitable peptides include, but are not limited to, C-peptide; glucagon-like peptide 1 (GLP 1) and all active fragments thereof; human amylin and synthetic forms of amylin, such as pramlintide; parathyroid hormone (PTH) and active fragments thereof (e.g. PTH.sub.1-34); calcitonin; human growth hormone (HGH); erythropoietin (EPO); macrophage-colony stimulating factor (M-CSF); granulocyte-macrophage-colony stimulating factor (GM-CSF); and interleukins. In the preferred embodiment the active agent is insulin.

C. Dosage Forms

The insulin loaded hydrogels may be administered in the form of a pharmaceutical composition as an admixture or mixture with one or more pharmaceutically acceptable carriers, excipients or diluents. Suitable dosage forms include powders, films, capsules and these formulations solubilized in an aqueous injectable excipient for administration by injection or pump.

The formulation are administered by injection, for example, subcutaneously, intramuscularly, or intradermally. In a preferred embodiment, the formulation is injected subcutaneously as a liquid suspension. In another embodiment, the formulation is formed by mixing a powdered active agent with a liquid diluent that contains a pharmaceutically acceptable liquid carrier and one or more solubilizing agents.

The ability of a particular insulin formulation to release insulin as a function of glucose levels can be assessed using standard techniques, such as in vitro glucose challenge experiments, dissolution experiments with release media containing glucose levels at 150 mg/dl or above, or in a diabetic animal model, such as, but not limited to, diabetic swine, diabetic mice, diabetic rat, or diabetic dog.

The insulin formulations are preferably formulated in dosage unit form for ease of administration and uniformity of dosage.

As would be appreciated by one of ordinary skill in this art, the carriers are chosen based on the route of administration as described below, the location of the target issue, the drug being delivered, the time course of delivery of the drug, etc. Suitable excipients include surfactants, emulsifiers, emulsion stabilizers, anti-oxidants, emollients, humectants, suspending agents, thickening agents, occlusive agents, preservatives, stabilizing agents, pH modifying agents, solubilizing agents, solvents, colorants, isotonicity providing agents and other excipients.

III. Method of Making the Compositions

A. Amphiphilic Peptides

The amphiphilic peptides can be synthesized using conventional synthesis techniques, for example, self-assembling peptides can be chemically synthesized or purified from natural or recombinantly-produced sources by methods well known in the art. These methods include exclusive solid phase synthesis, partial solid phase synthesis methods, fragment condensation, classical solution synthesis. Solid phase peptide synthesis procedures are well known in the art and further described by John Morrow Stewart and Janis Dillaha Young, Solid Phase Peptide Syntheses (2nd Ed., Pierce Chemical Company, 1984). The peptides described herein may be synthesized using an automated peptide synthesizer using standard chemistry such as, for example, t-Boc or Fmoc chemistry. Synthetic peptides can be purified by preparative high performance liquid chromatography

[Creighton T. (1983) Proteins, structures and molecular principles. WH Freeman and Co. N.Y.].

In a preferred embodiment, the amphiphilic peptide molecules are synthesized using solid phase peptide synthesis (SPPS). The N-terminus of the peptide can be modified with a glucose binding portion, using standard peptide coupling chemistry.

Self-assembly can be initiated using methods known in the art. For example, self-assembly can be initiated by the addition of an ionic solute or diluent to a peptide solution such as NaCl at a concentration of between approximately 5 mM and 5 M. Alternatively, self-assembly may be initiated or enhanced by introducing the peptides (whether dry, in a semi-solid gel, or dissolved in a liquid solution that is substantially free of ions) into a fluid (e.g., a physiological fluid such as blood) comprising such ions. Generally, self-assembly is expected to occur upon contacting the peptides with such a solution in any manner. Assembly time may be decreased in order to allow the material to intermingle with the underlying tissue or vessel before the material assembles.

A wide variety of ions, including anions and cations (whether divalent, monovalent, or trivalent), can be used. For example, one can promote a phase transition by exposure to monovalent cations such as $Li^+$, $Na^+$, $K^+$, and $Cs^+$, and the concentration of such ions required to induce or enhance self-assembly is typically at least about 5 mM, preferably at least about 10 mM, more preferably at least about 20 mM, and most preferably about 50 mM.

B. Insulin Loading

Insulin is loaded into the hydrogel either before, or after mixing the components which self-assemble into a hydrogel. In one embodiment, a hydrogel is incubated with an insulin solution to absorb the insulin.

C. Dosage Forms

Dosage forms may be formulated in a conventional manner using one or more physiologically acceptable carriers comprising known excipients and auxiliaries which facilitate processing into preparations which can be used pharmaceutically. Formulation of drugs is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980). Proper formulation is dependent upon the route of administration chosen.

In a preferred embodiment, the formulation is an injectable formulation. An injectable insulin formulation can be made by suspending the gel-encapsulated insulin in a diluent. The suspension is sterilized and filled in a vial suitable for unit or multiple injection dosing. Sterile injectable preparations may be formulated as known in the art. Among the acceptable vehicles and solvents that may be employed are water, Ringer's solution, U.S.P. and isotonic sodium chloride solution. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

IV. Methods of Using the Compositions

The formulation is administered as an admixture or mixture with one or more pharmaceutically acceptable carriers, excipients or diluents. Suitable dosage forms include powders, films, capsules and injectable formulations. Injectable formulations can be administered subcutaneously, intramuscularly, or intradermally. In preferred embodiment, the formulation is injected subcutaneously. In one embodiment, prior to injection, the formulation is in the form of a suspension.

In one embodiment, the formulation is an insulin formulation designed to release insulin into systemic circulation over time with a basal release profile following injection in a patient. In another embodiment, the formulation is designed to release insulin into systemic circulation over time with a non-basal release profile following injection in a patient. Exemplary non-basal release profiles include a regular human insulin release profile and a prandial release profile. In one embodiment the formulation is designed to release insulin into systemic circulation over time with a regular human insulin release profile following injection in a patient. In another embodiment, the formulation is designed to release insulin into systemic circulation over time with a prandial release profile following injection in a patient.

In theory, as the patient's blood glucose levels rise, the glucose binds to the glucose binding porting of the peptide hydrogel, disrupting interactions contributing to gel formation. The interaction with glucose leads to release from the insulin formulation in a blood glucose-dependent manner as shown in FIG. 1C.

In some embodiments, the insulin formulation is administered to patients who are not fully insulin dependent. In one embodiment, the formulation provides a sufficient amount of insulin to the patient during the day so that the patient does not require additional insulin-containing formulations to maintain his/her blood glucose levels within a safe range. The patient is typically not fully insulin dependent.

In another embodiment, the formulation is administered to a patient who is receiving intensive insulin therapy as one of the insulin-containing formulations administered to the patient during the day. Preferably the formulation delivers insulin to the patient with a basal release profile.

The present invention will be further understood by reference to the following non-limiting examples.

Example 1: Synthesis of Amphiphilic Peptides

An amphiphilic peptide molecule was synthesized using solid phase peptide synthesis (SPPS). The N-terminus was modified with 4-carboxylphenylboronic acid pinacol ester using standard peptide coupling chemistry. 1 wt % peptide gels were formed in a 0.1 M NaOH solution with the addition of 40 mM $CaCl_2$. The mixture was incubated for 1 hr at room temperature to allow for complete gelation. Transmission electron microscopy (TEM) of peptide solution validated the formation of typical bundled nanofibers generated by PAs.

Figure 2:
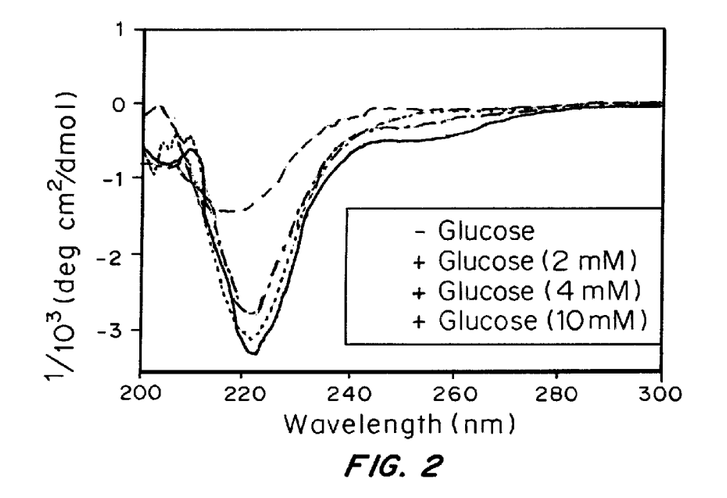
FIG. 2 is a graph showing changes in CD spectra of 1.0 nM peptide in PBS solution mixed with different glucose concentrations.

To demonstrate glucose responsiveness, the gel was incubated in a glucose solution. Incubation of the gel in a glucose solution overnight promoted the dissociation of the nanofibers and resulted in a free-flowing solution. The glucose-induced dissociation can also be confirmed by TEM. Short fibers and amorphous particles were clearly observed in samples in which the sample solution was pre-mixed with 400 mg/dL glucose and incubated for 3 hrs. Furthermore, the circular dichroism (CD) spectrum of the peptide solution revealed the Cotton effect at 220 nm, indicating the existence of beta sheet structure (FIG. 2). Upon the addition of glucose, the hallmark for beta sheet formation steadily decreased, consistent with the conclusions drawn above.

Example 2: In Vitro Insulin Release from Gel

Materials and Methods

Once the gel demonstrated the ability to undergo macroscopic changes in response to glucose, the utility of this material as an insulin delivery device was tested. The gel was formed and subsequently immersed in a FITC-conjugated insulin solution (1 mg/mL) to absorb insulin. After overnight incubation at room temperature, gel samples encapsulated with insulin were incubated with 1×PBS solutions with varying glucose levels, including a hyperglycemic level (400 mg/dL), a normal level (100 mg/dL) and a control level (0 mg/dL).

Results

As shown in FIG. 3, the accumulated insulin release plots determined by a fluorescence reader demonstrated that peptide gel can continuously release insulin in response to hyperglycemic glucose levels. In contrast, remarkably low release rates were detected when treated with the normal glucose level and control solution, which substantiate the glucose-responsive function of the peptide assemble hydrogel.

We claim:

1. Self-assembling glucose binding peptides comprising
   (a) a hydrophilic region comprising a charged segment which enhances solubility of the self-assembling peptide in an aqueous environment,
   (b) a hydrophobic region,
   (c) a beta-sheet forming region, and
   (d) an organic borate glucose binding moiety,
   wherein the hydrophilic and hydrophobic regions, present in distinct regions, sequentially along the backbone of the self-assembling peptide, are covalently linked via the beta-sheet forming region,
   wherein the self-assembling peptides are between six and about 200 α-amino acid residues,
   wherein the self-assembling peptides self-assemble under physiological conditions, of pH of approximately 7-7.5, to form a hydrogel, and
   wherein binding of glucose to the glucose binding moiety increases the permeability of the hydrogel.

2. The self-assembling glucose binding peptides of claim 1, wherein the hydrophilic region comprises charged amino acid residues.

3. The self-assembling glucose binding peptides of claim 1, wherein the hydrophobic region comprises side chains or amino acids forming a beta sheet structure.

4. The self-assembling glucose binding peptides of claim 1, wherein the organic borate is a phenyl borate.

5. The self-assembling glucose binding peptides of claim 1, wherein the glucose binding moiety is attached to the hydrophobic region.

6. The self-assembling glucose binding peptides of claim 1, wherein the beta-sheet forming regions of individual self-assembling peptides associate to form nanofibers.

7. The self-assembling glucose binding peptides of claim 1, wherein the beta-sheet forming region has about four to ten amino acid residues.

8. The self-assembling glucose binding peptides of claim 7, wherein the hydrophilic region has about two to seven amino acid residues.

9. The self-assembling glucose binding peptides of claim 8, the self-assembling peptide comprising between eight and about twenty-four α-amino acid residues.

10. A self-assembling glucose binding peptide having the chemical structure:

-continued

11. A hydrogel composition for delivering insulin or an insulin analog, comprising
Insulin or an insulin analog; and
self-assembling peptides comprising
(a) a hydrophilic region comprising a charged segment which enhances solubility of the self-assembling peptide in an aqueous environment,
(b) a hydrophobic region,
(c) a beta-sheet forming region,
(d) an organic borate glucose binding moiety,
wherein the hydrophilic and hydrophobic regions, present in distinct regions, sequentially along the backbone of the self-assembling peptide, are covalently linked via the beta-sheet forming region,
wherein the self-assembling peptides are between six and about 200 α-amino acid residues and
wherein the self-assembling peptides self-assemble under physiological conditions, of pH of approximately 7-7.5, forming a hydrogel,
wherein binding of glucose to the glucose binding moiety increases the permeability of the hydrogel, and
wherein the insulin or insulin analog is released.

12. The composition of claim 11, wherein the composition comprises insulin.

13. The composition of claim 11, wherein the insulin is selected from the group consisting of insulin lispro, insulin glulisine, insulin aspart, and insulin detemir.

14. The composition of claim 11, wherein the permeability of the hydrogel to insulin is increased when tissue glucose levels at physiological pH are increased.

15. The composition of claim 11, wherein the insulin or insulin analog is entrapped within the hydrogel.

16. A method for making a formulation for delivering insulin comprising self-assembling glucose binding peptides, wherein the self-assembling peptides each comprise:
(a) a hydrophilic region comprising a charged segment which enhances solubility of the self-assembling peptide in an aqueous environment,
(b) a hydrophobic region,
(c) a beta-sheet forming region, and
(d) an organic borate glucose binding moiety,
wherein the hydrophilic and hydrophobic regions, present in distinct regions, sequentially along the backbone of the self-assembling peptide, are covalently linked via the beta-sheet forming region,
wherein the self-assembling peptide comprises between six and about 200 α-amino acid residues, and
wherein the self-assembling peptides self-assemble under physiological conditions, of pH of approximately 7-7.5, to form a hydrogel, and
wherein binding of glucose to the glucose binding moiety increases the permeability of the hydrogel,
comprising adding insulin or insulin analog to a solution of the self-assembling peptides and
adding ions or changing pH to cause the self-assembling peptides to form a hydrogel entrapping the insulin or insulin analog in the hydrogel.

17. The method of claim 16, wherein the hydrophilic region has about two to seven amino acid residues.

18. The method of claim 17, the self-assembling peptide comprising between eight and about twenty-four α-amino acid residues.

19. A method of alleviating one or more symptoms of diabetes comprising administering to a diabetic individual an effective amount of the formulation of claim 11.

20. The method of claim 19 wherein the formulation is administered by subcutaneous injection.

21. The method of claim 16, wherein the insulin or insulin analog is entrapped within the hydrogel.

22. The method of claim 16, wherein the beta-sheet forming regions of individual self-assembling peptides associate to form nanofibers.

* * * * *